(12) United States Patent
Zhao

(10) Patent No.: US 7,527,970 B2
(45) Date of Patent: May 5, 2009

(54) METHOD OF IDENTIFYING ACTIVE CHROMATIN DOMAINS

(75) Inventor: Keji Zhao, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 340 days.

(21) Appl. No.: 11/087,896

(22) Filed: Mar. 23, 2005

(65) Prior Publication Data

US 2006/0084078 A1    Apr. 20, 2006

Related U.S. Application Data

(60) Provisional application No. 60/619,430, filed on Oct. 15, 2004.

(51) Int. Cl.
| | |
|---|---|
| *C12N 5/02* | (2006.01) |
| *C12N 5/06* | (2006.01) |
| *C12Q 1/68* | (2006.01) |
| *C12N 15/00* | (2006.01) |

(52) U.S. Cl. .......................... 435/325; 435/6; 435/326
(58) Field of Classification Search ........................ None
See application file for complete search history.

(56) References Cited

OTHER PUBLICATIONS

Fischer et al. Genomic Aberrations and Survival in Cutaneous T cell lymphomas. J. Invest. Dermatol. 122:579-586, 2004.*
Wells et al. Characterizing transcription factor binding sites using formaldehyde crosslinking and immunoprecipitation. Methods 26: 48-56, 2002.*
Boyd et al. Isolation and computer-aided characterization of Mmel, a Type II endorestriction nuclease from *Methylophilus methylotrophus*. Nuc. Acid Res. 14 (13): 5255-5274, 1986.*
Bernstein et al., *Proc. Natl. Acad. Sci. U.S.A.*, 99(13), 8695-8700 (2002).
Braunstein et al., *Gene Dev.*, 7, 592-604 (1993).
Brown et al., *Trends Mol. Med.*, 8(4), S43-S48 (2002).
Feinberg, *Seminars in Cancer Biology*, 14, 427-432 (2004).
Hake et al., *Brit. J. Cancer*, 90, 761-769 (2004).
Martone et al., *Proc. Natl. Acad. Sci. U.S.A.*, 100(21), 12247-12252 (2003).
Mueller et al., *Science*, 246, 780-786 (1989).
Patino et al., *Cir. Res.*, 91, 565-569 (2002).
Roh et al., *Genes Dev.*, 19, 542-552 (2005).
Roh et al., *Nature Biotechnol.*, 22(8), 1013-1016 (2004).
Roulet et al., *Nature Biotechnol.*, 20, 831-835 (2002).
Rundlett et al., *Nature*, 392, 831-835 (1998).
Saha et al., *Nat. Biotechnol.*, 19, 508-512 (2002).
Shi et al., *Cancer Res.*, 63, 2164-2171 (2003).
Suka et al., *Mol. Cell*, 8, 473-479 (2001).
Velculescu et al., *Cell*, 88, 243-251 (1997).
Velculescu et al., *Science*, 270, 484-487 (1995).
Vogelauer et al., *Nature*, 408, 495-498 (2000).
Wan et al., *Hum. Mol. Genet.*, 10(10), 1085-1092 (2001).

* cited by examiner

*Primary Examiner*—David Guzo
*Assistant Examiner*—Michele K. Joike
(74) *Attorney, Agent, or Firm*—Leydig, Voit & Mayer, Ltd.

(57) ABSTRACT

The invention provides a method of mapping DNA-protein interactions within a genome by fixing living cells to cross-link DNA and proteins, lysing the cells, and isolating chromatin by immunoprecipitation. DNA is purified and a SAGE protocol is performed on the purified DNA to produce GMAT-tag sequences, which are compared to a genomic sequence of the living cells to map DNA-protein interactions. The invention further provides a method of identifying an active chromatin domain and a method of identifying aberrant chromatin acetylation, wherein chromatin immunoprecipitation is performed using an antibody recognizing acetylated histone protein.

20 Claims, 7 Drawing Sheets

Genome

GMAT library

FIGURE 3B
FIGURE 3A
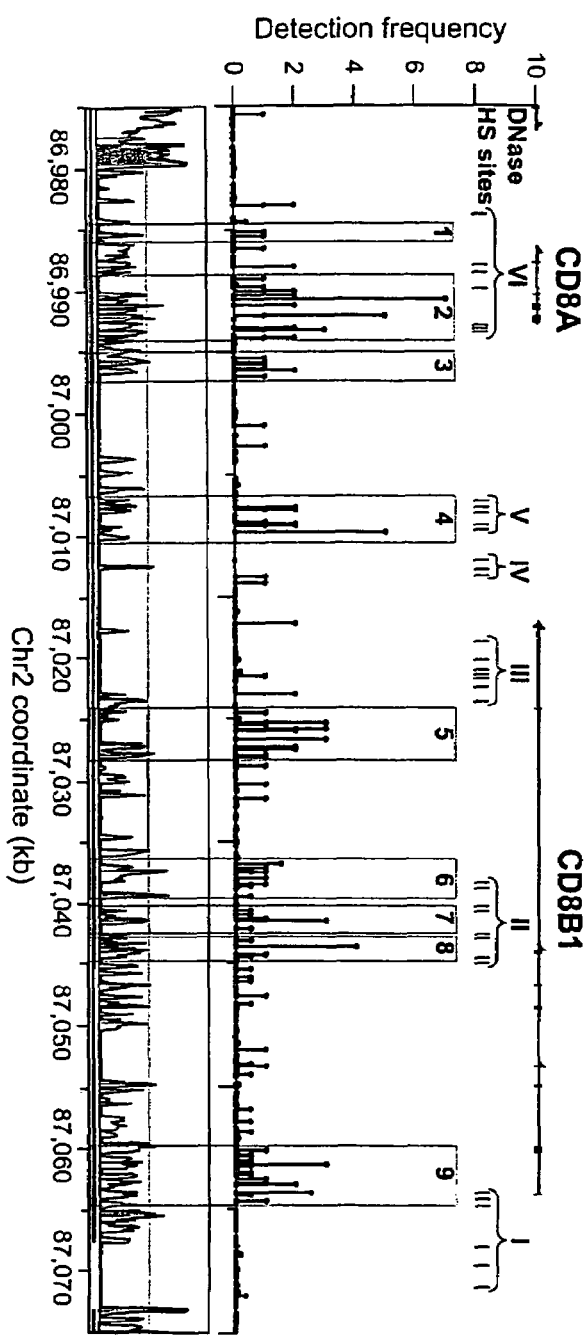
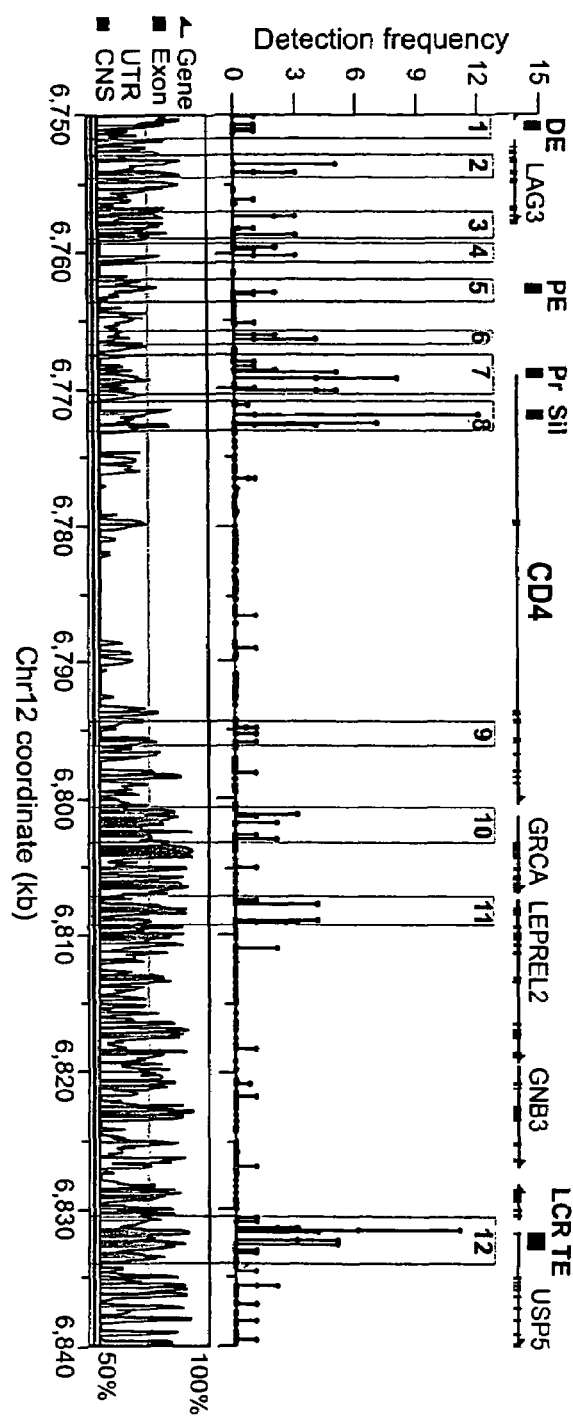

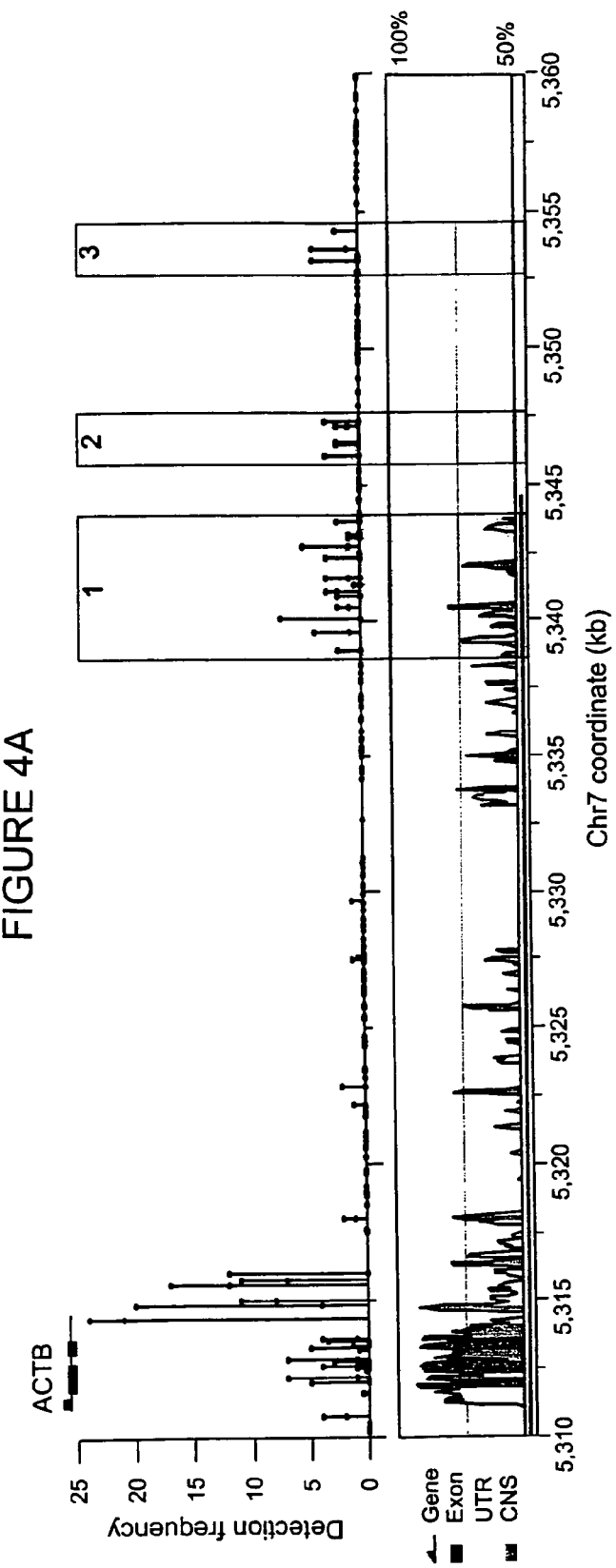
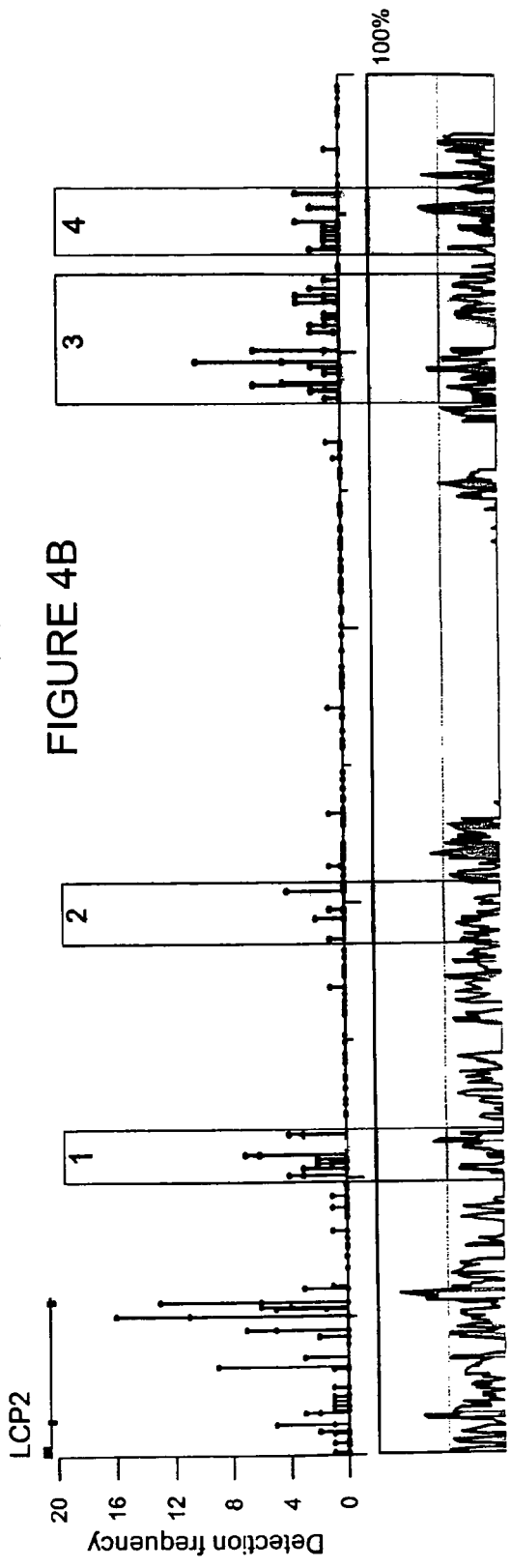
FIGURE 4A
FIGURE 4B

FIGURE 6A
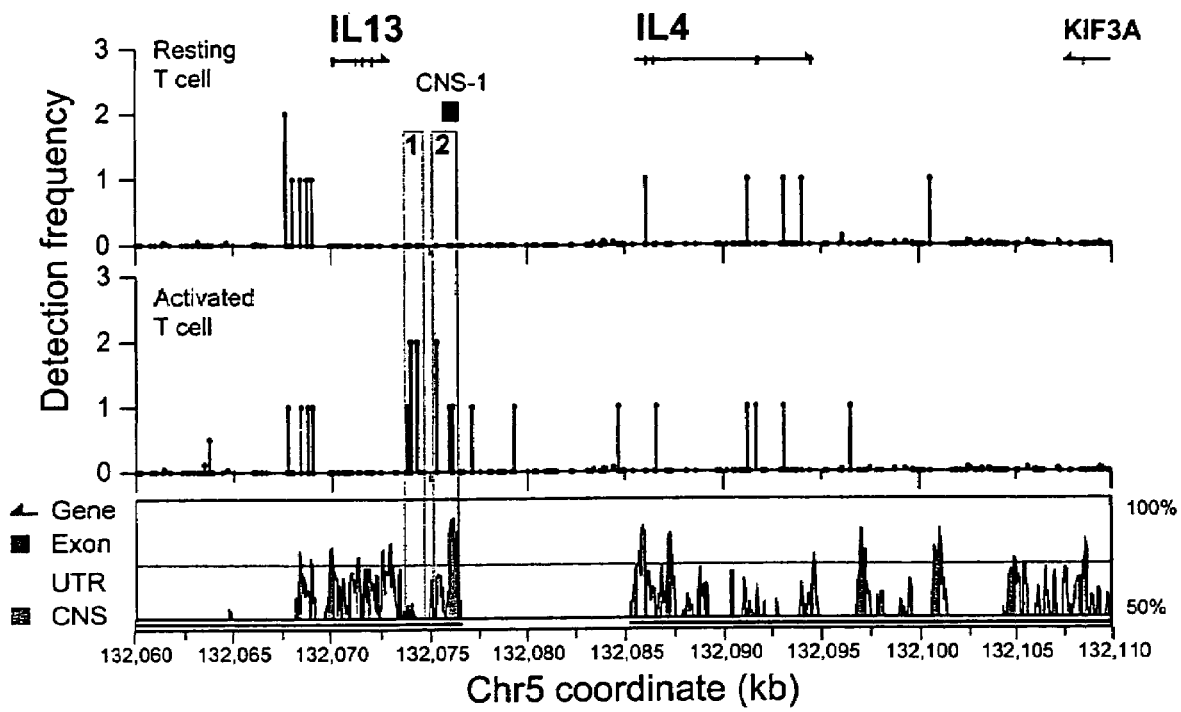
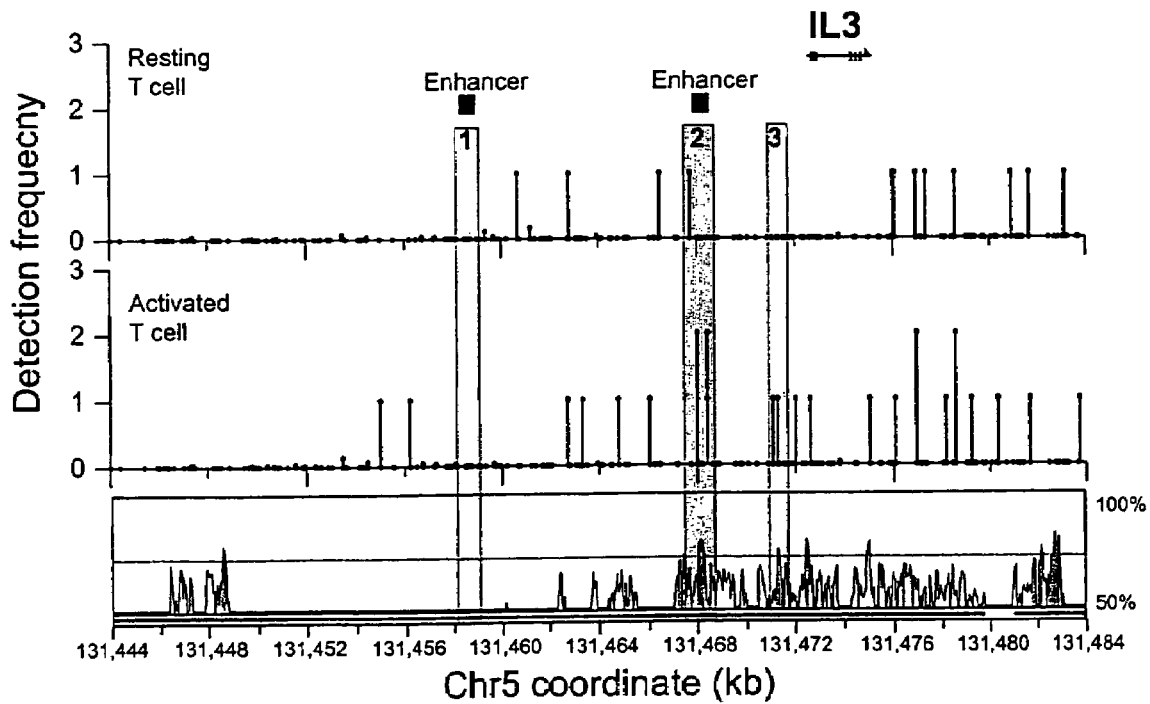
FIGURE 6B

METHOD OF IDENTIFYING ACTIVE CHROMATIN DOMAINS

CROSS-REFERENCE TO RELATED PATENT APPLICATIONS

This patent application claims the benefit of U.S. Provisional Patent Application No. 60/619,430, filed Oct. 15, 2004.

Incorporated by reference in its entirety herein is a computer-readable nucleotide/amino acid sequence listing submitted concurrently herewith and identified as follows: One 610 Byte ASCII (Text) file named "232477ST25TXT" created on Mar. 2, 2009.

FIELD OF THE INVENTION

This invention pertains to a method of identifying an active chromatin domain.

BACKGROUND OF THE INVENTION

Comparative genomics studies reveal the existence of long conserved noncoding sequences (CNSs) that are thought to play regulatory roles in the expression of mammalian genomes (Loots et al., *Science*, 288: 136-40 (2000); Dermitzakis et al., *Nature*, 420: 578-82 (2002)). Each type of nucleated cell of a mammal employs only a subset of the regulatory elements found in CNSs, thereby expressing only a subset of the genes of the mammalian cell at a given time. Many diseases and disorders are associated with abnormal gene expression, which can manifest as shifts in an affected cell's gene expression profile. Genetic modifications in a regulatory region of a CNS, i.e., changes in the regulatory sequence itself, can alter expression of an operably linked coding sequence. In addition, though all of the nucleated cells of a mammalian species have the same genome, every cell type has a different epigenome defined by posttranslational modifications of chromatin. Like changes to the actual regulatory sequence, post-translational modification of chromatin structure also can alter gene expression by, for example, allowing cellular proteins, such as transcription factors, access to DNA for transcription.

DNA is held in a chromatin structure, in part, by interactions with histone proteins. Histone modifications regulate the accessibility of chromatin and gene activity (reviewed in, for example, Kurdistani & Grunstein, *Nat. Rev. Mol. Cell. Biol.*, 4: 276-84 (2003); Berger, *Curr. Opin. Genet. Dev.*, 12: 142-48 (2002)). Histone acetylation is required for gene activation and cell growth (Durrin et al., *Cell*, 65: 1023-31 (1991); Megee et al., *Science*, 247: 841-45 (1990)). The mechanisms by which histone acetylation regulates chromatin structure and transcription are not fully understood; however, it is believed that the acetylation status of histone proteins signal factors that further regulate chromatin structure and gene activity (Strahl & Allis, *Nature*, 403: 41-45 (2000)). For example, the recruitment of Sir3 to form heterochromatin in yeast requires that the lysine at position 16 of the histone H4 protein is deacetylated (Hecht et al., *Nature*, 383: 92-96 (1996)). Therefore, acetylated histones may recruit and/or stabilize transcription factors and chromatin remodeling enzymes to their respective target sites in chromatin (Agalioti et al., *Cell*, 111: 381-92 (2002); Hassan et al., *Cell*, 104: 817-27 (2001)).

Delineating patterns of protein-DNA interactions and post-translational modifications to chromatin subunits would provide insight into the genomic positions of regulatory regions, the sequence of events leading to shifts in gene expression, and the type of protein-DNA interactions required for transcription. Currently, protein-DNA interactions are detected using marker and reporter proteins, which create a detectable signal when a desired protein binds its target sequence. Reporter assays require manipulation of the cellular environment. Thus, the results may not be predictive of the extent to which target proteins bind to target sequences in the absence of manipulation. Like reporter assays, electrophoretic mobility shift assays (EMSAs) provide little, if any, information regarding the genomic location of target sequences. Current methods also are time consuming and unspecific. DNA-protein interactions can be evaluated using chromatin immunoprecipitation (ChIP) in conjunction with DNA microarrays. However, currently available DNA microarrays generally cover only a small portion of a genome, which severely hinders analysis. In view of the above, there is a need in the art for an alternative method for identifying intracellular protein-DNA interactions. Ideally, the method can be extended to epigenomic research to analyze patterns of intracellular protein-DNA interactions associated with shifts in gene expression. The invention provides such a method. These and other advantages of the invention, as well as additional inventive features, will be apparent from the description of the invention provided herein.

BRIEF SUMMARY OF THE INVENTION

The invention provides a method of mapping DNA-protein interactions within a genome. The method comprises fixing living cells to cross-link DNA and proteins within the cells, lysing the cells to form a lysate, and isolating chromatin from the lysate by immunoprecipitation. The method further comprises purifying DNA from the immunoprecipitated chromatin and performing a serial analysis of gene expression (SAGE) protocol on the purified DNA to produce genome-wide mapping technique (GMAT)-tag sequences. The GMAT-tag sequences are compared to a genomic sequence of the living cells to map DNA-protein interactions with the genome of the cell.

The invention also provides a method of identifying an active chromatin domain. The method comprises fixing a sample of living cells to cross-link DNA and proteins within the cells. The method further comprises lysing the cells to form a lysate and applying an antibody that recognizes acetylated histone protein or a transcription factor. The chromatin is isolated by immunoprecipitation, and the DNA purified. A SAGE protocol is performed on the purified DNA to produce GMAT-tag sequences, which are compared to a genomic sequence of a control sample of living cells to identify an active chromatin domain. The inventive method can identify aberrant chromatin acetylation when the antibody recognizes acetylated histone protein H3 or H4, and the resulting GMAT-tag sequences are compared to a genomic sequence of a control sample of living cells and/or a diseased sample of living cells to identify aberrant chromatin acetylation in the tested cell sample.

In addition, the invention provides a method of preparing a plurality of DNA molecules. The method comprises fixing living cells to cross-link DNA and proteins, lysing the cells, and isolating chromatin by immunoprecipitation. The DNA is then purified from the immunoprecipitated chromatin. The purified, immunoprecipitated DNA is amplified to prepare a plurality of DNA molecules. The invention further provides a method of generating a genome-wide mapping library of nucleic acid sequences. The method comprises fixing living cells to cross-link DNA and proteins within the cells, lysing the cells, and isolating chromatin by immunoprecipitation.

DNA is purified from the immunoprecipitated chromatin and amplified. The amplified DNA, or a portion thereof, can be sequenced. The DNA sequences can be stored in a database to generate a genome-wide mapping library of nucleic acid sequences.

BRIEF DESCRIPTION OF THE DRAWINGS

FIG. 3A is a graph of acetylation data described in Example 3 for the CD4 locus wherein detection frequency (y-axis) is plotted against chromosome 12 coordinates (kb) (x-axis).

FIG. 3B is a graph of acetylation data described in Example 3 for the CD8 locus wherein detection frequency (y-axis) is plotted against chromosome 2 coordinates (kb) (x-axis).

FIG. 4A is a graph of acetylation data described in Example 3 for the β-actin gene (ACTB) locus wherein detection frequency (y-axis) is plotted against chromosome 7 coordinates (kb) (x-axis).

FIG. 4B is a graph of acetylation data described in Example 3 for the leukocyte protein gene (LCP) locus wherein detection frequency (y-axis) is plotted against chromosome 7 coordinates (kb) (x-axis).

FIG. 6A is a graph of acetylation data described in Example 3 for the IL13/IL4 gene locus wherein detection frequency (y-axis) is plotted against chromosome 5 coordinates (kb) (x-axis).

FIG. 6B is a graph of acetylation data described in Example 3 for the IL3 gene locus wherein detection frequency (y-axis) is plotted against chromosome 5 coordinates (kb) (x-axis).

DETAILED DESCRIPTION OF THE INVENTION

Figure 1:
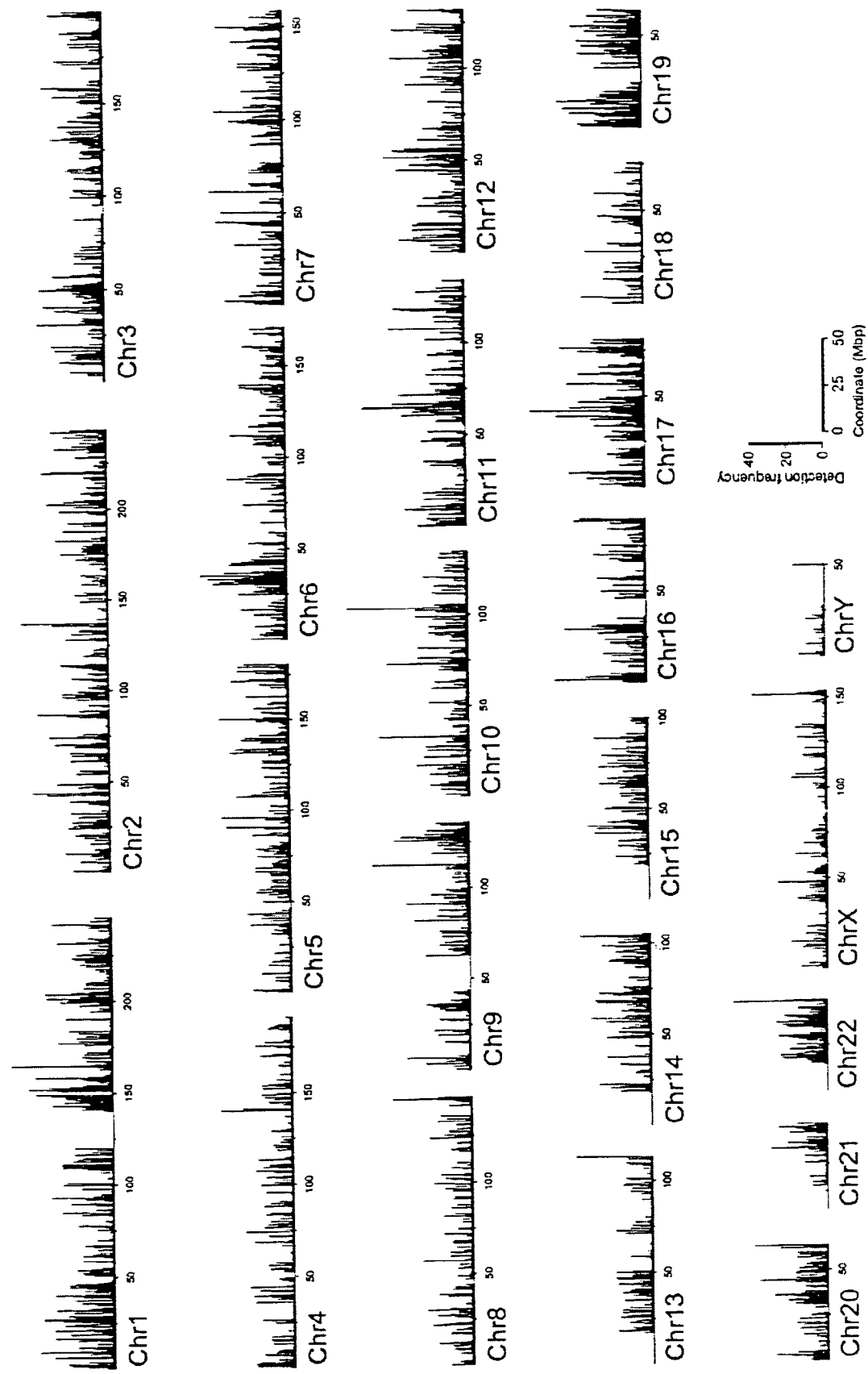
FIG. 1 is a graph of the number of GMAT-tag sequences that appears in the human genome (y-axis) plotted against the chromosome coordinate α-axis).

The invention enables mapping of intracellular protein-genomic DNA interactions. Thus, the inventive method is useful for characterizing portions of the genome, even CNSs having heretofore unknown function, and comparing protein-genomic DNA interactions between cell types or between diseased and normal cells. An advantage of the inventive method is the ability to specifically target DNA-binding proteins to identify protein binding sites within the genome. In fact, the method can distinguish between proteins based solely on post-translational modifications and, therefore, is a valuable tool in epigenetics research. Epigenetics involves not only the study of genome DNA sequences, but also chemical modifications of DNA (e.g., DNA methylation), proteins associated with DNA (e.g., histone proteins which, with DNA, form chromatin), and post-translational modifications of genome-associated proteins.

The inventive method is particularly useful for identifying active chromatin domains, i.e., sites of gene expression. In this context, regions of the genome can be identified which are bound by intracellular proteins associated with DNA transcription. Bound sequences can be mapped within the cellular genome for comparison with genomes from other cells and organisms. Histone proteins are integral in the early stages of gene expression, and their role is greatly influenced by post-translational chemical modifications to histone subunits. As such, post-translationally-modified histone subunits are optimal protein targets for the inventive method of identifying active chromatin domains.

The invention provides a method of mapping DNA-protein interactions within a genome. As described herein, the inventive method will be referred to as the genome-wide mapping technique (GMAT). The method comprises fixing living cells to cross-link DNA and proteins within the cells and lysing the cells to expose genetic material. Chromatin is isolated from the lysate via immunoprecipitation, and DNA is purified from the immunoprecipitated chromatin. The method further comprises performing a serial analysis of gene expression (SAGE) protocol on the purified DNA to produce GMAT-tag sequences, and comparing the obtained GMAT-tag sequences to a genomic sequence of the living cells to map DNA-protein interactions with the genome of the cell.

The invention can be used to detect or map protein-DNA interactions in any cell type including bacterial cells, yeast, plant cells, and animal cells (e.g., human cells). The cells can be obtained from cell culture or obtained from another source, such as a plant or animal. If obtained from an animal, such as a human, the cell sample can comprise any cell type or a mixture of cell types taken from the blood stream or any tissue. For example, the cell sample can comprise T cells, B cells, or a mixture of immune cells (e.g., T cells, B cells, natural killer (NK) cells, monocytes, and the like). The cells used in the inventive method can be normal, healthy cells or cells displaying an abnormal or diseased phenotype, such as cancer cells. The cells can be cancer cells of (i.e., located in) the oral cavity and pharynx, the digestive system, the respiratory system, bones and joints (e.g., bony metastases), soft tissue, the skin, breast, the genital system, the urinary system, the eye and orbit, the brain and nervous system (e.g., glioma), or the endocrine system (e.g., thyroid). Lymphoma cells (e.g., cells associated with Hodgkin's disease and Non-Hodgkin's lymphoma), multiple myeloma cells, or leukemia cells (e.g., acute lymphocytic leukemia, chronic lymphocytic leukemia, acute myeloid leukemia, chronic myeloid leukemia, and the like) also can be used in the context of the inventive method.

Preferably the cells used in the inventive method are living cells. Preparing a cell sample for use in the inventive method requires cross-linking DNA and proteins to ensure the protein-DNA complex remains intact during the lysing process. Any means of cross-linking DNA and proteins can be used in the context of the invention such as, for example, exposing intact cells to formaldehyde, potassium chromate, chromium (III) chloride hexahydrate, protein hydroperoxides, or x-rays. Likewise, any method of cell lysis is suitable for use in the inventive method so long as the method does not disrupt the protein-DNA cross-linked complexes. Mechanical disruption and detergents are often used for cell lysis and are suitable for use in the context of the invention. For example, a cross-linked cell sample can be washed, then sonicated to lyse the cells and break chromatin into manageable pieces. However, other methods of cell lysis are routinely used in molecular biology and are applicable to the method of the invention. While living, intact cells are preferred, the method also can be performed using cell lysate so long as the protein-DNA interactions are intact.

Once the cell sample is lysed, chromatin fractions are recovered via immunoprecipitation (i.e., chromatin immunoprecipitation (ChIP)). Immunoprecipitation entails applying an antibody specific for the protein linked to the cellular DNA and collecting the antibody-target protein-DNA complexes. Immunoprecipitation is generally described in *Antibodies: A Laboratory Manual*, Harlow and Lane, eds., Cold Spring Harbor Laboratories, Cold Spring Harbor, N.Y. (1988). The antibody can be monoclonal or polyclonal. Ideally, the antibody used in the inventive method is a monoclonal antibody that binds at least one protein cross-linked to the genomic DNA of the cell sample. Preferably, the antibody binds to a chromatin-modifying enzyme or a histone protein. The antibody can bind to any histone subunit, e.g., H1, H2A, H2B, H3, or H4. More preferably, the antibody binds to an acetylated histone protein, such as acetylated histone proteins H3 or H4. The acetylation of lysines 9 and 14 within the H3 amino acid sequence is important for activation of the human interferon-$\beta$ gene upon viral infection (Agalioti et al., *Cell*, 111: 381-92 (2002)). Genome-wide analyses in yeast and *Drosophila melanogaster* have correlated acetylation patterns with transcriptional activity (Kurdistani et al., *Cell*, 117: 721-33 (2004); Schubeler et al., *Genes Dev.*, 18: 1263-71 (2004)). Therefore, to identify active chromatin domains, the antibody used to immunoprecipitate DNA ideally recognizes an acetylated histone protein, such as acetylated histone protein H3 (e.g., acetylated at positions 9 and 14). Likewise, the antibody can bind to any of a number of chromatin-modifying enzymes, such as a histone acetylase (e.g., CBP/p300, PCAF, HAT1, HAT2, and the like).

Alternatively, to identify active chromatin domains, chromatin immunoprecipitation can be performed using antibodies that bind one or more transcription factors. Antibodies to any transcription factor can be used in the context of the invention. Ideally, the transcription factor binds DNA and not another transcription factor, although the method of the invention can be adapted to detect transcription factors that bind other transcription factors by cross-linking the protein-protein (i.e., transcription factor-transcription factor) complexes as well as the protein-DNA complexes. The transcription factor recognized by the immunoprecipitation antibodies preferably comprises a DNA binding domain; however, the method of the invention is not limited to a transcription factor comprising a particular type of DNA binding domain, e.g., leucine zipper, helix-loop-helix, zinc fingers, and the like. Exemplary transcription factors include, for example, Jun, Fos, Fra, Maf, NF-E2, AP-1, CREB, ubiquitous class A factors (e.g., E2A), MyoD, myogenin, c-Myc, EGR-1, WT-1, and NF-1.

The protein-DNA or protein-protein complexes can be disassembled using, for example, heat and/or a combination of Tris, EDTA, and detergent when cross-linking is effected by formaldehyde. Other methods of separating the complexes are available and can be readily determined by the ordinarily skilled artisan. The immunoprecipitating antibodies and the protein released from the protein-DNA complex or protein-protein complex can then be degraded by, for example, proteinase K digestion. The DNA fragments are then purified. Any appropriate method for purifying the DNA from the protein and antibody mixture can be used, such as those methods known in the art. For example, DNA can be purified by proteinase treatment, phenol/chloroform extraction, DNA purification kits (such as DNA purification kits available commercially) and precipitation. By "purified" is meant that the DNA is removed from all or part of the cell lysate and DNA binding proteins.

The purified DNA from the immunoprecipitation is characterized by SAGE. Using SAGE, a researcher can analyze a multitude of nucleic acids simultaneously. SAGE protocols are generally described in, for example, Velculescu et al., *Science*, 270: 484-487 (1995), and Velculescu et al., *Cell*, 88: 243-251 (1997). Historically, SAGE was used to characterize RNA transcripts. The inventive method uses a SAGE protocol to characterize genomic DNA by creating GMAT-tag sequences which are compared to the genomic sequence of the living cells. Location of the protein-DNA interactions within the genome are discovered by matching the DNA sequence of the GMAT-tag and the genomic sequence of a reference sample, such as the sample of living cells exposed to the inventive method. A map of the interactions can be compiled, which preferably comprises the location of at least one active chromatin domain.

The SAGE protocol applied to the purified DNA of the inventive method preferably comprises (i) ligating to the purified DNA a universal linker, (ii) cleaving the purified DNA with a first restriction enzyme to generate purified DNA fragments, (iii) ligating to the purified DNA fragments a non-phosphorylated linker comprising a recognition site for a second restriction enzyme, (iv) cleaving the purified DNA fragments with the second restriction enzyme, (v) dimerizing and amplifying the purified DNA fragments to generate DNA ditags, and (vi) cleaving the non-phosphorylated linker from the DNA ditags to generate GMAT-tag sequences.

If desired, the purified DNA can be amplified prior to ligating the universal linker. Otherwise, the first step of the SAGE protocol comprises ligating to the purified DNA a universal linker. In the context of the invention, a "universal linker" is an oligonucleotide applied to the purified DNA molecules and which comprises an affinity tag for adhering the purified DNA to a solid support, such as a bead (e.g., a magnetic bead), matrix, or platform. For example, the universal linker can be biotinylated such that the purified DNA can adhere to strepavidin beads. Other affinity tags that can be attached to the universal linker include, but are not limited to, protein A, an antigen, polyhistidine or metal ions, a FLAG epitope, and a hemagluttenin (HA) epitope. The universal linker can be attached to the purified DNA via a blunt end ligation reaction, or any other suitable means of ligation. Attachment of the DNA-universal linker to a solid support, in particular a magnetic bead, facilitates manipulation of the oligonucleotides. For example, the DNA molecules can be removed from a mixture using a magnet.

The SAGE protocol further comprises cleaving the purified DNA with a first restriction enzyme to generate purified DNA fragments. The first restriction enzyme can be selected based on the desired size of the purified DNA fragments and the non-phosphorylated linker used. For example, the first restriction enzyme can be selected to create a predetermined "sticky end" at the cleavage site for annealing the non-phosphorylated linker. Alternatively or in addition, a first restriction enzyme can be selected based on the frequency of the enzyme recognition sequence within the genome. Restriction enzymes whose recognition sequences are not often repeated in the genome will cut the genome in fewer pieces, resulting in larger purified DNA fragments. NlaIII is a suitable first restriction enzyme, although a myriad of others can be used and are known in the art.

Once the purified DNA is cleaved with the first restriction enzyme, a non-phosphorylated linker is ligated onto the cleaved DNA fragment. Surprisingly, the subsequent steps of the inventive method are significantly hindered when phosphorylated linkers are employed. Therefore, non-phosphorylated linkers are most desirable for use in the SAGE protocol after cutting the purified DNA with the first restriction enzyme. While one non-phosphorylated linker can be used in the method of the invention, using two or more different non-phosphorylated linkers can facilitate amplification of the GMAT-tag dimers. The non-phosphorylated linkers serve at least two functions in the context of the inventive method. First, the non-phosphorylated linker(s) comprises the recognition site (sequence) for a second restriction enzyme. Second, the non-phosphorylated linker can serve as a primer for PCR amplification of GMAT-tag dimers. With this in mind, the ordinarily skilled practitioner can design one or more non-phosphorylated linkers depending on the particular second restriction enzyme selected and PCR reaction.

Ideally, the first and second restriction enzymes are selected to create GMAT-tags comprising a sufficient number of nucleotides to enable precise mapping to the genome. A short oligonucleotide will map to several positions in the genome based on the frequency of the sequence, most of which may not correspond to a true protein binding sequence. However, a longer oligonucleotide, e.g., an oligonucleotide comprising 15 nucleotides or more, more uniquely and precisely identifies the positions of the DNA-protein interactions in the genome. Preferably, the GMAT-tag sequence is at least 10 nucleotides in length (e.g., 10, 15, 20, 25, 30, 35, or 40 nucleotides in length). More preferably, the GMAT-tag sequence is at least 15 nucleotides in length (e.g., 15, 20, or 25 nucleotides in length). Even more preferably, the GMAT-tag sequence is at least 20 nucleotides in length (e.g., 20, 21, 22, 23, 24, or 25 nucleotides in length).

To create GMAT-tags, the second restriction enzyme cleaves the purified DNA fragment downstream (or upstream) from the enzyme recognition site in the non-phosphorylated linker. Several restriction enzymes recognize and/or bind a nucleotide sequence while cutting the DNA molecule at another position away from the recognition site. Oftentimes, the exact number of nucleotides between the enzyme recognition site and cleavage site is known, making these enzymes particularly valuable for use in the inventive method. For example, MmeI cleaves DNA 21 base pairs from its recognition sequence. It is generally preferred to use a second restriction enzyme for which the span of nucleotides between the recognition site and cleavage site can be approximated. However, this is not required so long as the second restriction enzyme cleavage site is sufficiently distanced from the recognition site in the non-phosphorylated linker to create GMAT-tags capable of precisely mapping the DNA-protein interaction in the genome.

The purified DNA fragments are cleaved by the second restriction enzyme and are dimerized to generate DNA ditags. Ideally, the second restriction enzyme cuts the purified DNA fragments such that compatible ends of different DNA fragments are free to join together. However, the ordinarily skilled practitioner can ligate the cleaved DNA fragments together to form DNA ditags using any method which does not disrupt the continuity of the purified DNA fragment sequence. The DNA fragments can be amplified prior to dimerization and/or the DNA ditags can be amplified after dimerization has occurred. Amplification of the DNA ditags is facilitated by using primers to the non-phosphorylated linkers. Once the DNA ditags are amplified to the degree desired by the practitioner, the DNA ditags are cleaved to release the non-phosphorylated linkers. In a preferred embodiment, the DNA ditags are exposed to the first restriction enzyme, which removes the non-phosphorylated linkers from the ditag to generate GMAT-tag sequences. If desired, the GMAT-tag sequences can be concatenated and cloned.

The sequence of the GMAT-tag is compared to a genomic sequence of the living cells of the original cell sample. The GMAT-tag DNA molecules can be sequenced using any technique, such as the automated sequencing techniques known in the art. Once the DNA sequence of the GMAT-tag is obtained, the DNA sequence is matched to a sequence within the cellular genome, thereby identifying the position of the DNA-protein interaction. The genomes of many cell types and lower organisms are available on public and private genome databases. These databases allow mining of genomic DNA for sequences which match target DNA sequences, and can provide the position of matches with the genome. An exemplary search engine is BLAST available through the National Center for Biotechnology Information's GenBank. SAGE2000 software, available from Johns Hopkins University, also is a valuable tool for mapping protein-DNA interactions via GMAT. As merely an example of an outcome of the GMAT method, a map of acetylated histone binding to human T cell chromatin is illustrated in FIG. 1.

In addition, the invention provides a method of identifying active chromatin domains. The method comprises fixing a sample of living cells to cross-link DNA and proteins and lysing the cells. An antibody that recognizes acetylated histone protein or a transcription factor is applied to the lysed cells. The chromatin of the lysed cells is then isolated using immunoprecipitation, and the accompanying DNA is purified. The method further comprises performing a SAGE protocol on the purified DNA to produce GMAT-tag sequences, as described above. The GMAT-tag sequences are compared to a genomic sequence of a control sample of living cells to identify active chromatin domains. Preferably, the immunoprecipitation is performed using an antibody that binds an acetylated histone protein, such as histone subunit H3, the lysines of which at position 9 and/or 14 can be acetylated. By "control" sample of living cells is meant a sample of cells of the same origin as the sample of living cells exposed to the inventive method. Ideally, the control sample of living cells is collected from the same population of cells from which the sample of living cells exposed to the GMAT method was procured.

In one embodiment, the sample of living cells is taken from a patient (e.g., a human) and used in the inventive method. The GMAT-tag sequences are mapped to the genome of the living cells. Optionally, the method further comprises comparing the GMAT-tag sequences to a genomic sequence of a diseased sample of living cells to identify aberrant chromatin acetylation in the sample of living cells. The diseased sample of living cells comprises cells displaying an abnormal phenotype, and serves as a reference for identifying a pathological condition of the host based on chromatin acetylation. For example, the diseased sample of living cells comprises cancer cells, such as T cell leukemia cells or T cell lymphoma cells. Comparison of a test sample and a control or diseased sample of living cells can take many forms. In one context, the GMAT-tags are sequenced, and the sequence is mapped to the genome of cells from which the original living cell sample was obtained, a control sample (e.g., similar cells known to have a particular phenotype, such as non-cancerous immune cells), and/or a diseased sample (e.g., a pool of cancer cells). Active chromatin domains of cells in various states of disease, growth and replication, or infection can be identified. Alternatively, the active chromatin pattern of the sample of living cells can be compared to that of a control sample of living cells, which are known to be free of disease or infection such as, for example, the pattern of active chromatin domains of FIG. 1. The pattern of active chromatin domains can also be compared to the profile of diseased cells to determine if the original cell sample is abnormal. Thus, the inventive method can be used in a diagnostic assay for identifying diseased or infected host cells, such as cancer cells.

In view of the above, the invention also provides a method of identifying aberrant chromatin acetylation. The method comprises fixing a sample of living cells to cross-link DNA and proteins within the cells and lysing the cells. An antibody that recognizes acetylated histone protein H3 or H4 is applied to the lysed cells, allowing the cellular chromatin to be isolated via immunoprecipitation. The DNA is purified from the immunoprecipitated chromatin. The purified DNA is subjected to a SAGE protocol, which entails ligating to the purified DNA a universal linker, cleaving the purified DNA with a first restriction enzyme to generate purified DNA fragments, ligating to the purified DNA fragments a non-phosphorylated linker comprising a recognition site for a second restriction enzyme, cleaving the purified DNA fragments with the second restriction enzyme, dimerizing and amplifying the purified DNA fragments to generate DNA ditags, and cleaving the non-phosphorylated linker from the DNA ditags to generate GMAT-tag sequences. The method of identifying aberrant chromatin acetylation further comprises comparing GMAT-tag sequences to a genomic sequence of a control sample of living cells and/or a diseased sample of living cells to identify aberrant chromatin acetylation in the sample of living cells.

In addition to the above, the invention provides methods for preparing tools for genomic and epigenomic study. In particular, the invention provides a method of preparing a plurality of DNA molecules. The method comprises fixing living cells to cross-link DNA and proteins and lysing the cells. The cell's chromatin is isolated by immunoprecipitation, preferably using an antibody that binds acetylated histone protein or a transcription factor. The method further comprises purifying DNA from the immunoprecipitated chromatin, and amplifying the purified, immunoprecipitated DNA to prepare a plurality of DNA molecules. The plurality of DNA molecules obtained by the inventive method can be subjected to a SAGE protocol as described herein or another genomics assay or diagnostic test.

Likewise, the invention provides a method of generating a genome-wide mapping library of nucleic acid sequences. The method comprises fixing living cells to cross-link DNA and proteins within the cells and lysing the cells. The cell's chromatin is isolated by immunoprecipitation using, for example, antibodies to an acetylated histone protein or a transcription factor, and DNA is purified from the immunoprecipitated chromatin. The purified, immunoprecipitated DNA is amplified. The amplified DNA or a portion thereof can be sequenced, and the DNA sequences can be stored in a database to generate a genome-wide mapping library of nucleic acid sequences.

The following examples further illustrate the invention but, of course, should not be construed as in any way limiting its scope.

EXAMPLE 1

This example demonstrates use of the inventive method to map the genome-wide distribution of K9/K14 diacetylated histone H3-DNA interactions in resting and activated human T cells.

In vivo evidence regarding the function of histone acetylation in regulating gene expression stems from genetics studies in lower eukaryotic organisms such as yeast, which displays high levels of histone acetylation in the whole genome (Kurdistani & Grunstein, supra; Roh et al., *Nat. Biotechnol.*, 22: 1013-6 (2004)). Higher eukaryotic genomes differ from yeast in having much lower acetylation levels and more heterochromatic regions. Previous studies suggest that the whole active domain of chromatin is uniformly hyperacetylated when it is activated (Litt et al., *EMBO J*, 20: 2224-35 (2001)). The data below suggest that chromatin accessibility of a genetic locus is not caused by uniform hyperacetylation; instead, the openness is controlled by hyperacetylation of a limited number of regulatory elements.

The method described herein to detect global histone modifications does not depend on pre-selected DNA sequences. The method identifies a 21 bp sequence "tag" from purified chromatin. The 21 bp tag contains sufficient information to be mapped precisely in the human genome. The detection frequency of a tag in a genome-wide mapping technique (GMAT) library reflects directly the level of modification at the locus. Therefore, the level of histone modifications can be compared between different genetic loci. Histone modification was studied in primary human T cells because T cells have been used extensively as a model system for transcriptional regulation, and their biological functions have been thoroughly studied.

Human resting T cells were purified sequentially using lymphocyte separation medium (Mediatech, Herndon, Va.) and Pan T cell isolation kit II (Miltenyi Biotech, Auburn, Calif.). The final purity of T cells was over 98%. T cells were activated with 1 µg/ml of anti-CD3 and anti-CD28 monoclonal antibodies (BD PharMingen, San Diego, Calif.) for 24 hours.

Chromatin immunoprecipitation (ChIP) using anti-diacetylated K9/K14 histone H3 antibody (Upstate, Lake Placid, N.Y.) and generation of a GMAT library were performed as follows. T cells were lysed by vigorous vortexing with glass beads for 10 minutes. The lysate was sonicated, cooled on ice, and spun down using a microfuge. Two milliliters of the chromatin fraction and 8 ml of radioimmunoprecipitation (RIPA) buffer containing 140 mM NaCl were added to 400 µl of Sepharose protein A beads equilibrated in RIPA buffer. The mixture was incubated at 4° C. with rotation for 1 hour.

Five milliliters of precleared chromatin was added to 50 µl of Sepharose protein A beads. Twenty microliters of affinity-purified anti-ACH4 antibody was added to the reaction, and incubated at 4° C. overnight with rotation. The beads were washed twice with 5 ml of RIPA buffer (10 mM Tris/Ci, pH 7.5, 1 mM EDTA, 0.1% SDS, 0.1% sodium deoxycholate, 1% Triton X-100) containing 140 mM NaCl, and rotated for 10 minutes at room temperature. The beads were then washed twice with 5 ml of RIPA buffer containing 300 mM NaCl, and rotated again for 10 minutes. The beads were washed again, twice, with 5 ml of LiCi buffer (Tris-EDTA buffer (TE) (1×), 0.25M LiCi, 0.5% Nonidet p40 (NP40), 0.5% Na-deoxycholate), and rotated for 10 minutes. The beads were then washed twice with 5 ml of TE (1×), and rotated for 10 minutes. The beads were resuspended in 200 µl of TE (1×), 5 µl of 10% SDS, and 10 µl of 10 mg/ml Proteinase K, mixed well, and incubated at 65° C. overnight.

The supernatant was collected the next day, and the beads were washed with 100 µl of TE (1×). The wash liquid was combined with the supernatant. DNA was extracted by treatment with phenol-$CHCl_3$ and precipitation with 1 µl of 20 mg/ml glycogen, 30 µl of 3M NaOAc (pH 5.2), and 700 µl of ethanol. The resulting pellet was washed once with 70% EtOH and briefly air dried. The DNA was resuspended in 30 µl of TE (1×).

To 13 µl of DNA, 2 µl of 10× EcoPol buffer, 3 µl of 1 mM dNTPs, and 2 µl of Klenow enzyme (10 units) were added. The mixture was incubated at 37° C. for 20 minutes. The reaction was stopped by adding 80 µl of TE (1×) and phenol-$CHCl_3$ extraction. The DNA was precipitated by adding 10 µl of 3M NaOAc (pH 5.2), 1 µl of 20 mg/ml glycogen, and 250 µl of EtOH. The resulting pellet was resuspended, and the universal linker was attached (5'-biotinylated WL1 (5'-biotin-GCGGTGACCCGGGAGATCTGAATTC-3' (SEQ ID NO: 1)) and non-biotinylated WL2 (5'-GAATTCAGATC-3') (SEQ ID NO: 2)). The mixture was heated at 95° C. for 5 minutes, then cooled to 4° C. slowly (about 2 hours).

The linkers were ligated by adding 5 µl of 10× ligation buffer, 5 µl of the annealed WL1 (biotin)+WL2, and 2 µl of T4 DNA ligase (NEB, 400 units/µl) to 38 µl of DNA. The mixture was incubated at 14° C. for 16 hours. The DNA was purified via phenol-$CHCl_3$ extraction and precipitation. The DNA was resuspended in 10 µl of TE (1×), and amplified via PCR using the 5' biotinylated WL1 as the primer.

The DNA was cleaved with a first restriction enzyme, NlaIII. The cleaved DNA was purified by phenol-$CHCl_3$ extraction and precipitation with glycogen. To 58 µl of DNA, 8 µl of 10× ligation buffer was added, and the DNA was dispensed into two tubes. To the mix was added 5 µl of 8 µM annealed Linker 1 (tube 1) and 5 µl of 8 µM annealed Linker 2 (tube 2). Linker 1 and linker 2 were prepared according to Saha et al., *Nature Biotechnology*, 20: 508-512 (2002), except that the linkers were not phosphorylated to avoid self-ligation. The tubes were heated at 50° C. for 2 minutes and incubated at room temperature for 10 minutes. To each tube was added 2 µl of T4 DNA ligase, and the mixtures were allowed to incubate at 16° C. overnight. The ligation mixtures were combined and purified by phenol-$CHCl_3$ extraction and precipitation.

The DNA was added to 100 µl of Dynabeads M-280 (Strepavidin). The beads were washed with 200 µl of binding buffer (TE (1×), 1 M NaCl). Additional binding buffer and 20 µl DNA were added and allowed to incubate for 15 minutes at room temperature with occasional mixing. The supernatant was discarded, and the beads were washed with binding buffer and TE (1×). The bound DNA was digested immediately with a second restriction enzyme, MmeI. The supernatant was collected, and the DNA was purified by extraction with phenol-$CHCl_3$. The DNA was precipitated with 2 µl of 20 mg/ml glycogen, 30 µl of 3M NaOAc (pH 5.2), and 825 µl of ethanol. The resulting pellet was washed with 70% ethanol, and the DNA resuspended in 9 µl of 1× ligation buffer. T4 DNA ligase (New England Biolabs, 1 µl of 400 units/µl) was added, and the mixture was incubated at 16° C. overnight.

The PCR amplification of the ditags, NlaIII digestion, isolation and concatenation of ditags, and cloning using pZeroI were performed as set forth in Saha et al., supra. A theoretical reference library of 21 bp sequence tags was derived from the UCSC July 2003 human sequence (hg16) using SAGE2000 ver. 4.5 software (Johns Hopkins Oncology Center). The GMAT library was generated by extracting 21 bp tags from raw sequencing data files using the SAGE2000 software. All other calculations and analyses were performed using in-house Practical Extraction and Report Language (PERL) programs. Detection frequency was determined by normalizing tag count to the genomic copy number. Tag density was calculated by dividing the detection frequency by the number of expected NlaIII sites in a 50 bp window.

Table 1A summarizes the 21 bp tag distribution in the human genome and in GMAT libraries. The calculated column shows the calculated number of the 21 bp tags derived from NlaIII cleavage of human genome sequence. The detected column indicates the number of the 21 bp tags detected in the GMAT library from the resting and activated T cells. "Total tags" represent the total number of the 21 bp tags existing in the human genome or detected in the libraries. "Unique tags" indicate the number of the 21 bp tags whose sequence is found only once in the human genome. "Repetitive tags" indicate the number of the 21 bp tags whose sequence is found two or more times in the human genome. "Tag kinds" represent the number of the 21 bp tags including both the unique tags and repetitive tags, all of which are counted once even if they appear more than once in the human genome.

TABLE 1A

Tag Distribution in the Human Genome

| | | Detected in GMAT Library | |
|---|---|---|---|
| | Calculated in the Genome | Resting T cells | Activated T cells |
| Total Tags | 24,577,210 | 803,439 | 761,624 |
| Tag Kinds | 18,559,414 | 414,655 | 425,762 |
| Unique Tags | 17,686,797 (72%) | 670,073 (83%) | 626,692 (82%) |
| Repetitive Tags (2-91,831) | 6,890,413 (28%) | 133,366 (17%) | 134,932 (18%) |

As shown in Table 1A, the human genome contains a total of 24,577,210 tags, which represent 18,559,414 kinds of tags (or different 21 bp sequences). By sequencing 32,544 GMAT clones, a total of 803,439 tags was obtained, which represent 414,655 kinds of tags. Therefore, 2.2% of the tag kinds in the human genome were detected in the GMAT library. To determine if the genome was sufficiently covered, the level of H3 K9/K14 acetylation was quantified in resting T cells using ChIP as described (Litt et al., supra). The results showed that about 1.2% of nucleosomes in total chromatin is associated with K9/K14 acetylated H3. Since the repetitive sequences, which make up about 40% of the human genome, are associated with hypoacetylated histone H3 (Table 1B), about 2% of the unique sequences in the genome are associated with the acetylated histone. In Table 1B, "repeat number in genome" indicates the number of times a 21 bp-tag appears in the human genome. Repeat number "1" indicates a unique sequence. Repeat number "2" indicates a sequence that is found two times in the genome. "Calculated tag kinds" indicate the total number of tag kinds with the same copy number in the human genome. "Detected tag kinds" indicate the total number of tag kinds with the same copy number detected in the GMAT library. The "percentage of detection" was calculated by dividing the detected tag kinds in the GMAT library by the calculated tag kinds in the human genome. The data summarized in Table 1B is consistent with the data that 2.1% of unique tags were detected in the GMAT library. The sequencing, therefore, covered most of the acetylated regions.

TABLE 1B

Repetitive Sequences Are Associated with Lower Levels of Histone H3 Acetylation in Resting T cells

| Repeat Number in Genome | Calculated Tag Kinds | Detected Tag Kinds | Percentage of Detection |
|---|---|---|---|
| 1 | 17,686,797 | 365,250 | 2.1% |
| 2 | 517,461 | 3,497 | 0.7% |
| 3 | 133,541 | 517 | 0.4% |
| 4 | 64,570 | 169 | 0.3% |
| 5-100 | 151,854 | 182 | 0.1% |
| 101-91,831 | 5,191 | 0 | 0 |

Approximately 2.1% of the unique sequences (1 repeat) in the genome were detected in the GMAT library while the percentage of detection decreased as the repetitiveness (repeat number) increased, indicating that higher repetitive sequences are associated with lower levels of the histone H3 acetylation (see Table 1B). Since the repetitive sequences were not associated with significant levels of H3 acetylation and the repetitive tags that are associated with acetylated H3 could not be mapped precisely in the human genome, only the unique tags were analyzed further.

A total of 670,073 tags derived from unique sequences was detected (Table 1A). The detection frequency of the tags in the GMAT library ranged from 1 to 65 times (Table 1C). In Table 1C, "detection frequency" indicates the number of times a tag was detected in the GMAT library. Single copy tags are those with a detection frequency of 1. Approximately 40.7% of these tags were detected only once (single-copy tag) and 59% were detected multiple times in the library (Table 1C).

TABLE 1C

The Detection Frequency of Unique Tags Varies Widely

| Detection Frequency | Number of Tags | Percentage in Library |
|---|---|---|
| 1 | 272,477 | 40.7% |
| 2 | 81,334 | 12.1% |
| 3 | 49,404 | 7.4% |
| 4 | 38,864 | 5.8% |
| 5 | 31,675 | 4.7% |
| 6-10 | 99,963 | 14.9% |
| 11-65 | 96,356 | 14.4% |

To confirm that the tags detected in the library represent the levels of histone modification, and are not derived from contamination during ChIP experiments, about 100 tags were randomly picked and analyzed by quantitative PCR using specific primers. A 200 bp to 300 bp fragment of DNA containing the selected tag was amplified from the ChIP DNA in the presence of $\alpha$-$^{32}$P(dCTP) for phosphoimager analysis. The band intensity was normalized to the band intensities of two control regions from the β globin domain. A value of 1.5-fold or more was considered positive. The analysis confirmed that all of the tags that were detected two times or more were associated with H3 acetylation. In Table 1D, "distance to the nearest tag" indicates how far a neighboring detected tag is located. The "percentage of detected tags" indicates the percentage of the tags categorized by the distance to a nearest detected tag. "Number of tested tags" indicates the number of positive tags and total number of tested tags (bracket), respectively, in the PCR analysis.

TABLE 1D

Most Tags are Truly Positive Tags

| | Distance to Nearest Tag | Percentage of Detected Tags | Number of Tested Tags | Positive (%) |
|---|---|---|---|---|
| Multiple-Copy Tags | na | 59.3 | 15 (15) | 100.0 |
| Single-Copy Tags | 0-5 | 32.5 | 42 (57) | 73.7 |
| | >5 | 7.9 | 9 (25) | 36.0 |

For the single-copy tags, 91% were positive when the distance to the nearest detected tag was within 1 kb, and 86% were positive when the distance was between 1 to 5 kb. When the nearest detected tag was found at a distance of 20 to 30 kb, the ratio of positive tags decreased to 50% (Table 1D). However, only 0.9% of the tags fell into this category. Therefore, all of the multiple-copy tags and most of the single-copy tags detected in the GMAT library were associated with the acetylated histone H3.

To reconfirm that the GMAT-tags were derived from acetylated histone proteins but not from non-acetylated regions by contamination, the β globin domain was examined as a control. The β globin domain is not expressed and exists as condensed chromatin in resting T cells. Approximately 250 bp region encompassing a single or multicopy acetylation tag site was amplified. Two regions of β-globin domain were used as controls. The PCR products were labeled by incorporating $\alpha$-$^{32}$P(dCTP) in the reaction and were separated on a denaturing polyacrylamide gel for quantification using the phosphorimager (Molecular Dynamics, CA, USA). The 120 kb region contained 1,016 predicted tags. Only three tags from this region were detected in the GMAT library. It cannot be conclusively determined if the three tags represent true low levels of acetylation or background. However, the data indicate that the background level was very low, and most of the tags detected in the library were derived from the specific association with acetylated H3.

Based on the sequence information, the GMAT tags were mapped onto the 24 chromosomes in the human genome (FIG. 1). The x-axis indicates the chromosomal coordinates of the tags, and the y-axis indicates the detection frequency (number of times detected) for a tag in the GMAT library. Thus, this example demonstrates a method of mapping protein-DNA interactions in the genome of human T cells. The data demonstrate that acetylated H3 was not evenly distributed on chromosomes. Instead, there appears to be clusters of the tags and large chromosomal regions with low levels of tags, indicating that there are chromatin domains that are highly or poorly acetylated. For example, chromosome 13 contains several large gaps due to low or no histone acetylation.

EXAMPLE 2

This example demonstrates the ability of the inventive method to identify active chromatin domains.

Figure 2A:
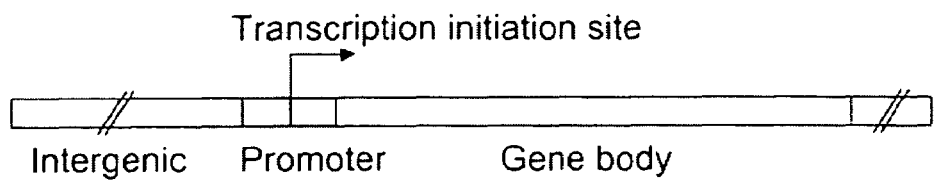
FIG. 2A is a schematic showing the human genome arbitrarily separated into three parts: 2 kb-promoter regions, intergenic regions, and gene body regions.
Figure 2B:
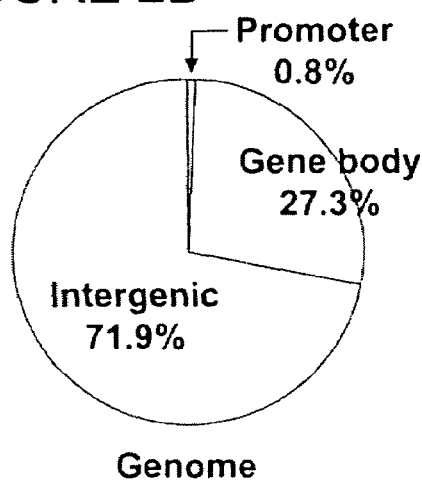
FIG. 2B is a graph illustrating the calculated percentage of promoter regions, intergenic regions, and gene body regions in the genome.
Figure 2C:
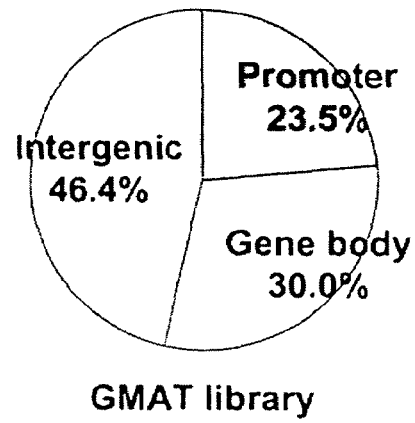
FIG. 2C is a graph illustrating the percentage of GMAT-tags detected in the GMAT library from each region.

The materials and methods described in Example 1 were used to confirm that H3 acetylation is a hallmark of active sites in chromatin. To determine if H3 acetylation is biased toward any functional regions in the human genome, the human genome was arbitrarily defined as consisting of three parts: (a) a 2 kb-promoter regions including 1 kb upstream and 1 kb downstream of the transcription initiation site, (b) gene body regions including introns and exons, (c) and intergenic regions (FIG. 2A). The 2 kb-promoter region makes up 0.8% of the genome (FIG. 2B). The gene body and intergenic regions make up 27.3% and 71.9% of the genome, respectively. Interestingly, 23.5% of the tags detected in the GMAT library were derived from the promoter region, and 30.0% and 46.4% of the tags were from the gene body and intergenic regions, respectively (FIG. 2C). These results indicate that the distribution of the acetylated H3 is biased toward the promoter region in the genome.

Figure 2D:
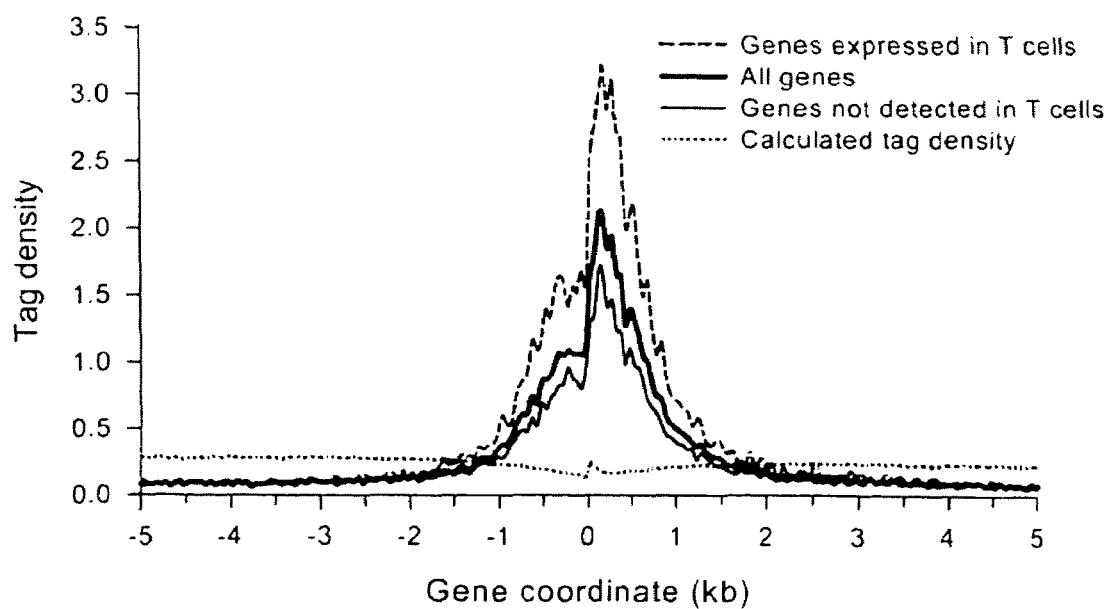
FIG. 2D is a graph illustrating the alignment of a 10 kb region of 22,000 genes relative to their transcription initiation sites (x-axis) plotted against tag density obtained by normalizing the total number of detected GMAT-tags with the number of expected NlaIII site in a 50 bp-window (y-axis), as described in Example 2.

FIG. 2D illustrates tag density within the genome found by aligning 21,355 annotated genes relative to their transcription initiation sites. The tag density was derived by normalizing the detected number of tags in the GMAT library to the number of expected NlaIII sites in a 50 bp-window across a 10 kb region. The calculated tags are distributed evenly across the whole region. Interestingly, a significant peak of tags was detected in the GMAT library in the 2 kb-promoter region, as revealed by the heavy black line in FIG. 3C representing data for all of the genes. These data indicate that the acetylation level of active promoters is twice as high as that of silent promoters. It is noteworthy that the 1 kb 5'-untranslated region of the genes has the highest level of the acetylation.

Looking to FIG. 2D, high levels of acetylation were detected only in the promoter region, even in active genetic loci. Detectible levels of acetylation were not observed in transcribed regions of active genes. This finding contradicts the general belief that chromatin accessibility and gene expression of an active domain is controlled by increased acetylation throughout the whole domain. To gain more insights, high-resolution maps of a few active loci including TCR, CD4, and CD8 were examined. For example, the CD4 domain spans 90 kb of chromatin from its 3' locus control region (LCR) to its 5' distal enhancer (DE) (Ellmeier et al., Annu. Rev. Immunol., 17: 523-54 (1999); Siu, Semin. Immunol., 14: 441-51 (2002)). Only 15% of its chromatin was associated with acetylated H3. The acetylation occurred mainly within regulatory elements. Most of the transcribed regions in the domain did not have detectible levels of acetylation (FIG. 3). Thus, active domains are not uniformly hyperacetylated, suggesting that histone acetylation controls chromatin accessibility in a different way than what is currently believed.

The results of this example confirm that the inventive method can be used in the identification of active chromatin domains. It is generally believed that chromatin accessibility at an active genetic locus is controlled by uniform histone hyperacetylation throughout the whole chromatin domain (Litt et al., EMBO J, 20: 2224-35 (2001)). At least 10,000 to 15,000 genes are expressed in any human tissues, which occupy about 15% of the human genome. However, the results described herein show that only 1.2% of the human chromatin is acetylated. Therefore, this level of acetylation does not allow all of the active chromatin domains to be uniformly highly acetylated. Indeed, most of intergenic and transcribed regions of active chromatin are not acetylated at any detectible levels. Instead, high levels of acetylation are only detected in the functional regulatory elements including promoters, enhancers, LCRs, and insulators. The data suggest that the chromatin accessibility and expression of a gene is not controlled by uniform hyperacetylation of the whole domain; instead, the openness is controlled by hyperacetylation of a number of regulatory elements, which is sufficient to actively limit the spreading neighboring heterochromatin.

EXAMPLE 3

This example demonstrates a method of identifying acetylation islands using the materials and methods described in Examples 1 and 2.

Examination of high-resolution maps generated in Example 2 revealed clusters of two or more GMAT-tags along the chromatin fiber signifying acetylation ("acetylation islands") (highlighted in FIGS. 3 and 4). An acetylation island was defined by the following criteria: (i) it is composed of tags from more than two adjacent NlaIII sites; (ii) the detection frequency of all the tags is more than or equal to one; and (iii) neighboring acetylation islands are separated by greater than 500 bp. A total of 21,481 and 25,332 acetylation islands were detected in intergenic and transcribed regions, respectively.

Comparative genomics studies have identified about 270,000 conserved noncoding sequences (CNSs) in the human and mouse genomes (Hardison, Trends Genet., 16: 369-72 (2000)), which are believed to be regulatory elements in the mammalian genomes. For comparative analysis of human and mouse genomes, graphic alignments were adopted from the Vista Browser (Couronne et al., Genome Res., 13: 73-80 (2003)) that shows human gene information and sequences of more than 50% homology with mouse genome assembly.

FIG. 3A summarizes data with respect to the CD4 locus. The upper panel shows the acetylation data, above which gene positions and known functional regulatory elements are indicated. The lower panel shows the Vista human and mouse sequence comparison. The abbreviations listed on FIG. 3A are as follows: "DE" is distal enhancer; "PE" is proximal enhancer; "Pr" is promoter; "Sil" is silencer; "LCR" is locus control region; and "TE" is thymocyte enhancer. FIG. 3B summarizes data regarding the CD8A locus. The positions of the six clusters of DNase hypersensitive sites (HS) are indicated below the genes. As shown in FIGS. 3A and 3B, most of the acetylation islands are associated with CNSs that revealed by Vista analysis illustrated in the lower part of FIGS. 3A and 3B.

FIG. 4A summarizes the analysis of the β-actin locus. The upper panel shows the acetylation data as in FIG. 1. The lower panel shows the Vista human and mouse sequence comparison. The position and orientation of the β-actin gene (ACTB) is indicated in the middle section of the figure. The percentage on the right to the vista data indicates the degree of conservation between human and mouse. Three acetylation islands in the upstream intergenic region are present. FIG. 4B summarizes similar analysis with respect to the locus for the leukocyte protein gene (LCP).

Comparative analysis of human chromosome 21 with syntenic regions of the mouse genome has revealed 2,262 CNSs in the intergenic regions (Dermitzakis et al., Nature, 420: 578-82 (2002)). Two hundred eighty two acetylation islands in the intergenic regions were identified on the chromosome. Comparison between the CNSs and acetylation islands indicates that there are 187 acetylated CNSs, which accounts for 66% of the acetylation islands and 8.3% of CNSs. Extrapolating these results to the whole genome predicts that a total of about 30,000 acetylation islands are associated with CNSs.

The significant colocalization of acetylation islands with CNSs suggests that the acetylation islands may represent functional regulatory elements in T cells. Therefore, acetylation islands were examined with respect to known regulatory elements in T cells. CD4 is a critical T cell co-receptor that assists antibody production. DNase hypersensitive sites (HS)

mapping combined with transgenic studies has identified several regulatory elements that collectively mediate the specific expression of the CD4 gene (reviewed by Ellmeier et al., *Annu. Rev. Immunol.*, 17: 523-54 (1999); Siu, *Semin. Immunol.*, 14: 441-51 (2002)). Strong acetylation was detected in the promoter (FIG. 3A, Box #7). Interestingly, the proximal enhancer, which is conserved between human and mouse and is located 6.5 kb upstream of its transcription initiation site in human, is colocalized with an acetylation island (FIG. 3A, Box #5). The distal enhancer located upstream of the LAG3 gene also was acetylated (FIG. 3A, Box #1). The CD4 gene also is regulated by a locus control region (LCR) and a thymocyte enhancer located 30 kb downstream of the CD4 gene with several intervening genes. A significant acetylation island was detected in the LCR/TE region (FIG. 3A, Box #12). Besides the known regulatory elements, several other significant acetylation islands were detected within the locus (FIG. 3A, Boxes #2, #3, #4, #6, #9, #10, and #11).

The CD8α and CD8β co-receptors play critical roles in mediating cell killing. The minimal functional elements of the human CD8 genes, which render their specific expression, are contained in a 95 kb region (Kieffer et al., *J. Immunol.*, 159: 4907-12 (1997)). Six clusters of DNase HSs are present in the locus (Kieffer et al., *J. Immunol.*, 168: 3915-22 (2002)), as summarized in FIG. 3B. Most of these HS sites coincided well with significant acetylation islands. However, the HS cluster III was not co-localized with any significant acetylation islands. Instead, a significant acetylation island was detected about 5 kb away from HS III (FIG. 3B, Box #5). Since the expression level of the CD8 genes contained in the 95 kb region varies depending on the integration site, it does not contain an LCR, which suggests that an LCR may be located outside of the region. Examining the acetylation map revealed a highly acetylated region and a TCR signaling-induced island, 100 kb and 40 kb downstream of the CD8α gene, respectively.

Figure 5:
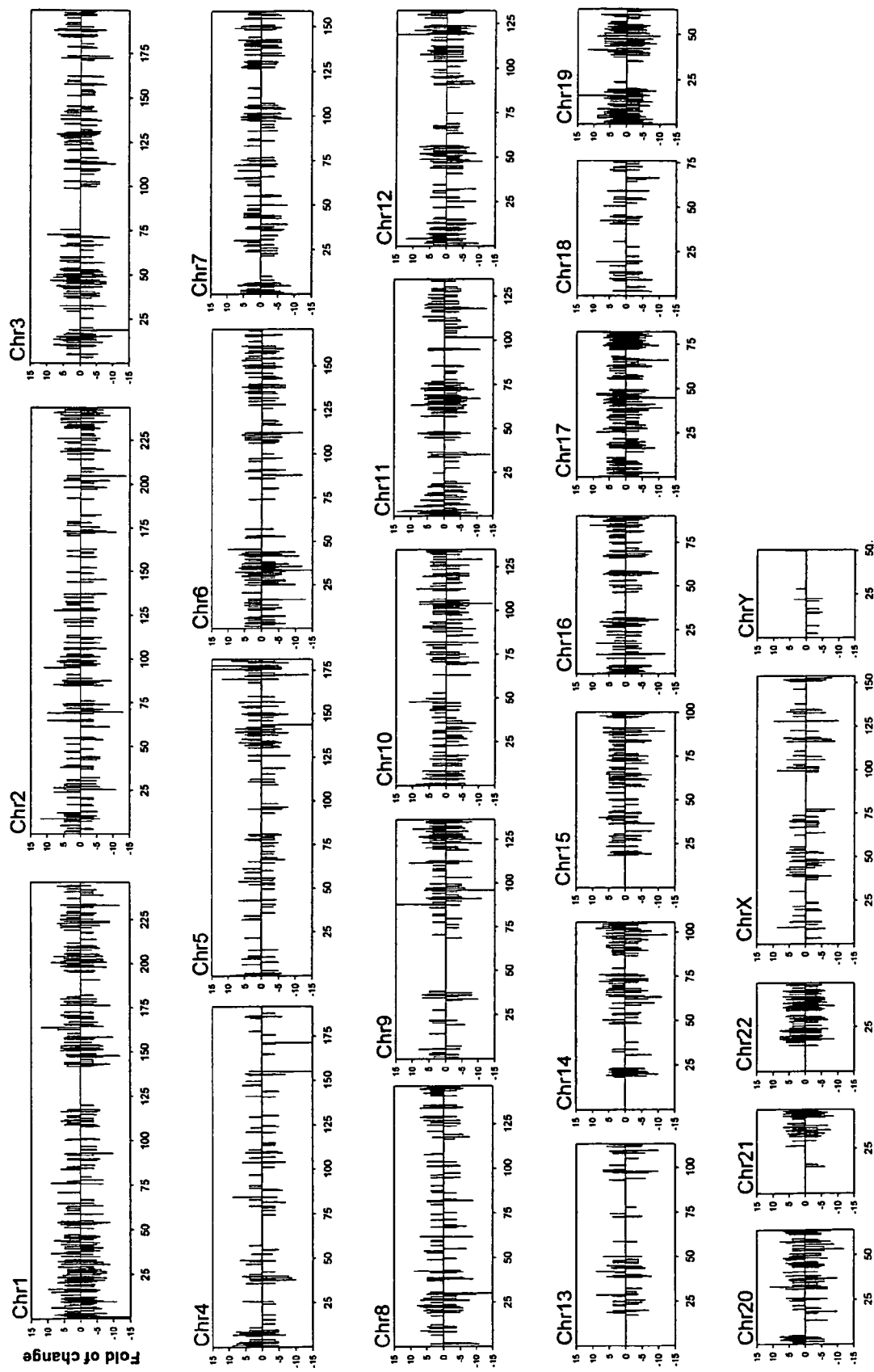
FIG. 5 is an illustration plotting fold-change of average tag densities from activated and resting T cells (y-axis) against chromosome coordinates (x-axis).

TCR signaling induces thousands of genes required for cellular differentiation and immunologic functions, accompanied by massive chromatin decondensation (Crabtree, *Science*, 243: 355-61 (1989)). Histone H3 acetylation of T cells after 24 hours of TCR signaling was analyzed to identify cis regulatory elements that initiate the global chromatin remodeling upon T cell activation (Table 1A). Changes in acetylation levels between the resting and activated T cells were analyzed by comparing the average tag density, which is obtained by dividing the total number of detected tags by the number of NlaIII sites in the region, within a 3 kb window. Changes of three times or more were plotted along chromosome coordinates (FIG. 5). The analysis revealed that increased acetylation was detected at 4,045 loci and decreased acetylation was detected at 4,178 loci, indicating that the TCR signaling induced a genome-wide acetylation change.

To determine if the acetylation islands induced by TCR signaling are involved in T cell activation, the CNS-1 sequence at the Th2 cytokine locus that harbors the coordinately expressed genes IL5, IL13, and IL4 was examined. It was demonstrated previously that CNS-1, located between the IL13 and IL4 genes, is required for the coordinated expression of the three cytokine genes in Th2 cells (Loots et al., supra). The inventive method indicates that CNS-1 was not acetylated before TCR stimulation (FIG. 6A, upper panel). In FIG. 6A, the upper and middle panels show the acetylation data from resting and activated T cells, respectively. The lower panel shows the Vista human and mouse sequence comparison. The gene locations are indicated above the acetylation data. Interestingly, an acetylation island (FIG. 6A, Box #2) was induced over the CNS-1 region by TCR signaling (FIG. 6A, middle panel), suggesting that histone acetylation may be involved in the function of CNS-1 in regulating the cytokine gene expression. It is noteworthy that another acetylation island (FIG. 6A, Box #1) was induced immediately next to CNS-1, suggesting that more regulatory elements in this region may participate the regulation of the cytokine gene.

Another well characterized locus is the IL-3 gene that can be activated in T cells via TCR signaling pathways through two enhancers located 4.5 kb and 14 kb upstream of its promoter (Hawwari et al., *J. Immunol.*, 169: 1876-86 (2002)) (FIG. 6B). In FIG. 6B, the acetylation data and vista sequence analysis are shown as in FIG. 7A. The two enhancers identified previously also are indicated above the acetylation data. Low levels of acetylation was detected in the 4.5 kb region in resting T cells (FIG. 6B, upper panel, Box #2). Upon TCR signaling, the acetylation levels increased significantly in the 4.5 kb and proximal promoter regions (FIG. 6B, middle panel, Boxes #2 and #3). Acetylation at the −14 kb region was not observed before and after TCR stimulation (FIG. 6B, Box #1), which is consistent with the observation that this enhancer may not be functional in peripheral blood T cells. These results indicate that the acetylation islands identified by this analysis play important regulatory roles in the T cell activation.

Figure 7A:
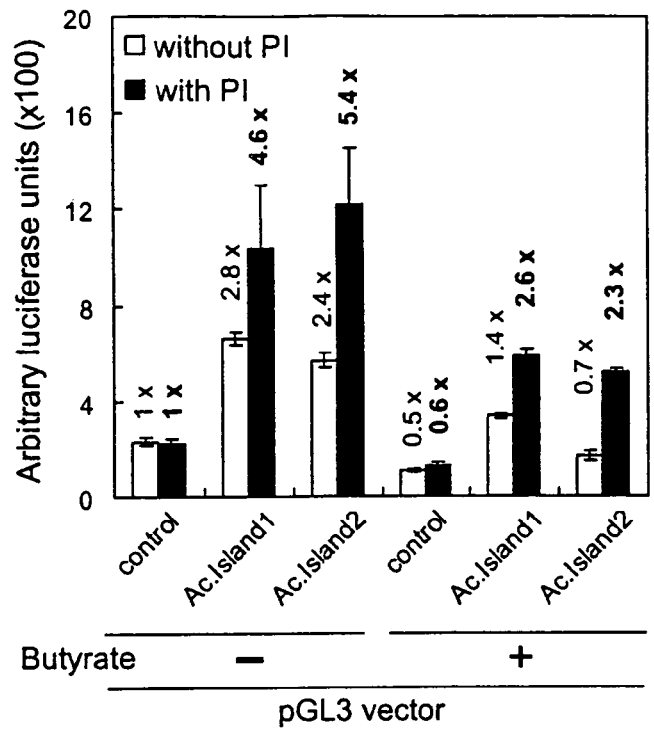
FIG. 7A is a graph comparing the activities of acetylation island 1 and acetylation island 2, encoded by the pGL3 vector, in the presence and absence of butyrate (x-axis), as expressed as arbitrary luciferase units (y-axis).
Figure 7B:
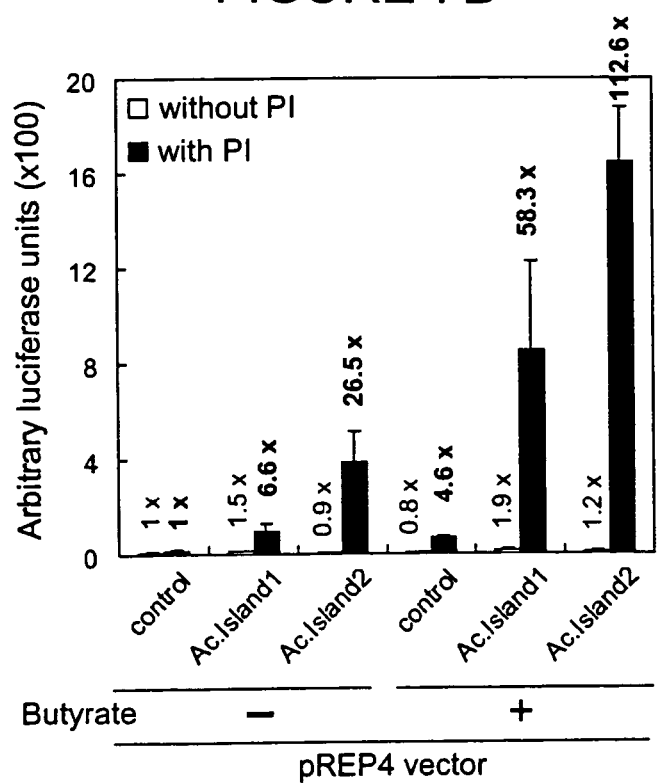
FIG. 7B is a graph comparing the activities of acetylation island 1 and acetylation island 2, encoded by the pREP4 vector, in the presence and absence of butyrate (x-axis), as expressed as arbitrary luciferase units (y-axis).

As suggested by the above analyses, acetylation islands may be functional regulatory elements. To demonstrate if the data can predict regulatory elements, the activities of acetylation islands 1 and 2 of the IL13/IL4 locus (FIG. 6A) were tested in a reporter assay. The 1.5 kb DNA containing acetylation islands 1 and 2 were inserted upstream of a minimal GM-CSF1 promoter in pGL3 vector. The constructs were transfected into Jurkat cells for 48 hours, followed by stimulation with 1 µg/ml ionomycin and 10 ng/ml PMA for 15 hours. In case of butyrate treatment, 10 mM of butyrate was added at the same time with ionomycin and PMA. The luciferase activity was analyzed with the dual luciferase system from Promega. "PI" in FIGS. 7A and 7B refers to PMA and ionomycin treatment. As shown in FIG. 7A, acetylation island 2 containing CNS-1 sequence activated the GM-CSF1 promoter in pGL3 vector 2.4-fold in Jurkat cells, even though it does not form a regular chromatin structure in transiently transfected cells. TCR signaling further activated the promoter two-fold. Interestingly, acetylation island 1, which is located next to CNS-1 and is not conserved between human and mouse, had a similar activity as acetylation island 2. These sequences were cloned into the episomal pREP4 vector, which replicates and forms a regular chromatin structure in cells. Acetylation islands 1 and 2 did not significantly increase the promoter activity without TCR stimulation (FIG. 7B). Interestingly, in the presence of TCR signaling, acetylation islands 1 and 2 activated the promoter 6.6- and 26.5-fold, respectively. Treatment with butyrate, which increases acetylation levels by inhibiting histone deacetylase activities, dramatically enhanced the activities of both acetylation islands 1 and 2 in pREP4 but not in pGL3 vector (see FIGS. 7A and 7B). These results indicate that the acetylation islands are indeed epigenetic marks for functional regulatory elements.

In summary, comparison of the human and mouse genomic sequences reveals the existence of 270,000 conserved non-coding sequences which may function to direct the expression programs of the genomes. However, even though all of the nucleated human cells have the same genome, each cell type has a different "epigenome." Each cell type expresses a different set of genes, which requires a different set of regulatory elements. The 46,813 acetylation islands identified in Examples 1-3 represent the functional regulatory network required for the expression programs in T cells by their colocalization with known DNase HSs and regulatory elements, by their association with CNSs, and their activities in the reporter assays. The data provide valuable information for further identification of cis regulatory elements and for elucidation of regulatory mechanisms of transcription of almost every gene expressed in T cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of mapping DNA-protein interactions within a genome, wherein the method comprises:
    (a) fixing living cells to cross-link DNA and proteins within the cells,
    (b) lysing the cells to form a lysate comprising chromatin,
    (c) isolating the chromatin from the lysate by immunoprecipitation,
    (d) purifying DNA from the immunoprecipitated chromatin,
    (e) performing a serial analysis of gene expression SAGE protocol on the purified DNA to produce SAGE-tag sequences, and
    (f) comparing genome-wide mapping technique GMAT-tag sequences to a genomic sequence of the living cells to map DNA-protein interactions with the genome of the cell.

2. The method of claim 1, wherein immunoprecipitation is performed with antibodies to acetylated histone protein.

3. The method of claim 2, wherein the antibodies recognize acetylated H3 protein.

4. The method of claim 3, wherein the antibodies recognize H3 protein acetylated at positions 9 and 14.

5. The method of claim 4, wherein mapping the DNA-protein interactions identifies at least one active chromatin domain within the genome.

6. The method of claim 1, wherein the immunoprecipitation is performed with antibodies to a transcription factor.

7. The method of claim 1, wherein performing the SAGE protocol comprises:
   (i) ligating to the purified DNA a universal linker,
   (ii) cleaving the purified DNA with a first restriction enzyme to generate purified DNA fragments,
   (iii) ligating to the purified DNA fragments a non-phosphorylated linker comprising a recognition site for a second restriction enzyme,
   (iv) cleaving the purified DNA fragments with the second restriction enzyme,
   (v) dimerizing and amplifying the purified DNA fragments to generate DNA ditags,
   (vi) cleaving the non-phosphorylated linker from the DNA ditags to generate GMAT-tag sequences.

8. The method of claim 7, wherein the purified DNA fragments comprise at least 15 nucleotides.

9. The method of claim 7, wherein the second restriction enzyme cleaves the purified DNA fragments at least 15 nucleotides from the recognition site.

10. A method of identifying an active chromatin domain, wherein the method comprises:
   (a) fixing a sample of living cells to cross-link DNA and proteins within the cells,
   (b) lysing the cells to form a lysate comprising chromatin,
   (c) applying to the lysate an antibody that recognizes acetylated histone protein or a transcription factor,
   (d) isolating the chromatin from the lysate by immunoprecipitation,
   (e) purifying DNA from the immunoprecipitated chromatin,
   (f) performing a SAGE protocol on the purified DNA to produce SAGE-tag sequences, and
   (g) comparing GMAT-tag sequences to a genomic sequence of a control sample of living cells to identify an active chromatin domain.

11. The method of claim 10 further comprising (h) comparing GMAT-tag sequences to a genomic sequence of a diseased sample of living cells to identify aberrant chromatin acetylation in the sample of living cells.

12. The method of claim 10, wherein performing the SAGE protocol comprises:
   (i) ligating to the purified DNA a universal linker,
   (ii) cleaving the purified DNA with a first restriction enzyme to generate purified DNA fragments,
   (iii) ligating to the purified DNA fragments a non-phosphorylated linker comprising a recognition site for a second restriction enzyme,
   (iv) cleaving the purified DNA fragments with the second restriction enzyme,
   (v) dimerizing and amplifying the purified DNA fragments to generate DNA ditags, and
   (vi) cleaving the non-phosphorylated linker from the DNA ditags to generate GMAT-tag sequences.

13. The method of claim 12, wherein the antibodies recognize acetylated histone protein.

14. The method of claim 13, wherein antibodies recognize acetylated H3 protein.

15. The method of claim 14, wherein the antibodies recognize H3 protein acetylated at positions 9 and 14.

16. The method of claim 12, wherein the purified DNA fragments comprise at least 15 nucleotides.

17. The method of claim 12, wherein the second restriction enzyme cleaves the purified DNA fragments at least 15 nucleotides from the recognition site.

18. The method of claim 12, wherein the diseased sample of living cells comprises cancer cells.

19. The method of claim 18, wherein the cancer cells are T cell leukemia cells or T cell lymphoma cells.

20. A method of identifying aberrant chromatin acetylation, wherein the method comprises:
   (a) fixing a sample of living cells to cross-link DNA and proteins within the cells,
   (b) lysing the cells to form a lysate comprising chromatin,
   (c) applying to the lysate an antibody that recognizes acetylated histone protein H3 or H4,
   (d) isolating the chromatin from the lysate by immunoprecipitation,
   (e) purifying DNA from the immunoprecipitated chromatin,
   (f) performing a SAGE protocol on the purified DNA to produce GMAT-tag sequences, wherein the SAGE protocol comprises
      (i) ligating to the purified DNA a universal linker,
      (ii) cleaving the purified DNA with a first restriction enzyme to generate purified DNA fragments,
      (iii) ligating to the purified DNA fragments a non-phosphorylated linker comprising a recognition site for a second restriction enzyme,
      (iv) cleaving the purified DNA fragments with the second restriction enzyme,
      (v) dimerizing and amplifying the purified DNA fragments to generate DNA ditags, and
      (vi) cleaving the non-phosphorylated linker from the DNA ditags to generate GMAT-tag sequences, and
   (g) comparing GMAT-tag sequences to a genomic sequence of a control sample of living cells and/or a diseased sample of living cells to identify aberrant chromatin acetylation in the sample of living cells.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial
<220> FEATURE:
<223> OTHER INFORMATION: Synthetic

<400> SEQUENCE: 1
gcggtgaccc gggagatctg aattc                                    25

<210> SEQ ID NO 2
<211> LENGTH: 11
<212> TYPE: DNA
<213> ORGANISM: Artificial
<220> FEATURE:
<223> OTHER INFORMATION: Synthetic

<400> SEQUENCE: 2
gaattcagat c                                                   11
```